(12) United States Patent
Runge et al.

(10) Patent No.: US 6,458,745 B1
(45) Date of Patent: Oct. 1, 2002

(54) SOLID PHYTOSANITARY AGENT

(75) Inventors: Frank Runge, Maxdorf; Georg Konrad Zwissler, Bad Dürkheim; Dieter Horn, Heidelberg; Lutz End, Mannheim; Reiner Kober, Fussgönheim; Karl-Heinrich Schneider, Kleinkarlbach; Reinhold Stadler, Kirrweiler; Hans Ziegler, Mutterstadt; Wilhelm Rademacher, Limburgerhof; Oskar Schmidt, Schifferstadt; Volker Harries, Frankenthal; Reinhold Saur, Böhl-Iggelheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/284,258

(22) PCT Filed: Oct. 8, 1997

(86) PCT No.: PCT/EP97/05535

§ 371 (c)(1),
(2), (4) Date: Apr. 9, 1999

(87) PCT Pub. No.: WO98/16105

PCT Pub. Date: Apr. 23, 1998

(30) Foreign Application Priority Data

Oct. 11, 1996 (DE) .......................... 196 41 939
Oct. 17, 1996 (DE) .......................... 196 42 879

(51) Int. Cl.[7] .......................... A01N 3/02; A01N 63/00; A01N 25/00
(52) U.S. Cl. .......................... 504/116; 504/118; 424/405
(58) Field of Search .......................... 504/118, 116; 424/405

(56) References Cited

U.S. PATENT DOCUMENTS

| 4,244,836 A | 1/1981 | Frensch et al. ............. 252/316 |
| 4,522,743 A | 6/1985 | Horn et al. ................. 252/311 |
| 5,133,908 A | 7/1992 | Stainmesse et al. ......... 264/4.1 |
| 5,703,010 A | 12/1997 | Heinrich et al. ............ 504/116 |

FOREIGN PATENT DOCUMENTS

| WO | 95/03356 | | 2/1995 |
| WO | 9503356 | * | 2/1995 |

OTHER PUBLICATIONS

Database WPI, Derwent Publications Ltd, AN 86–011602, XP 002053975 (JP 60237007).

* cited by examiner

Primary Examiner—Alton Pryor
(74) Attorney, Agent, or Firm—Keil & Weinkauf

(57) ABSTRACT

A solid crop protection composition consisting essentially of
a) one or more predominantly amorphous crop protection active ingredients which are solid per se and have solubility in water of less than 500 mg/l at 25° C. and
b) a coating enclosing component (a).

18 Claims, 6 Drawing Sheets

Chlorpyrifos

Ascorbylpalmitat

Lactose

Gelita Sol P

Gelatine B 100 Bloom

RuD 55-95-05

SOLID PHYTOSANITARY AGENT

Figure 1:
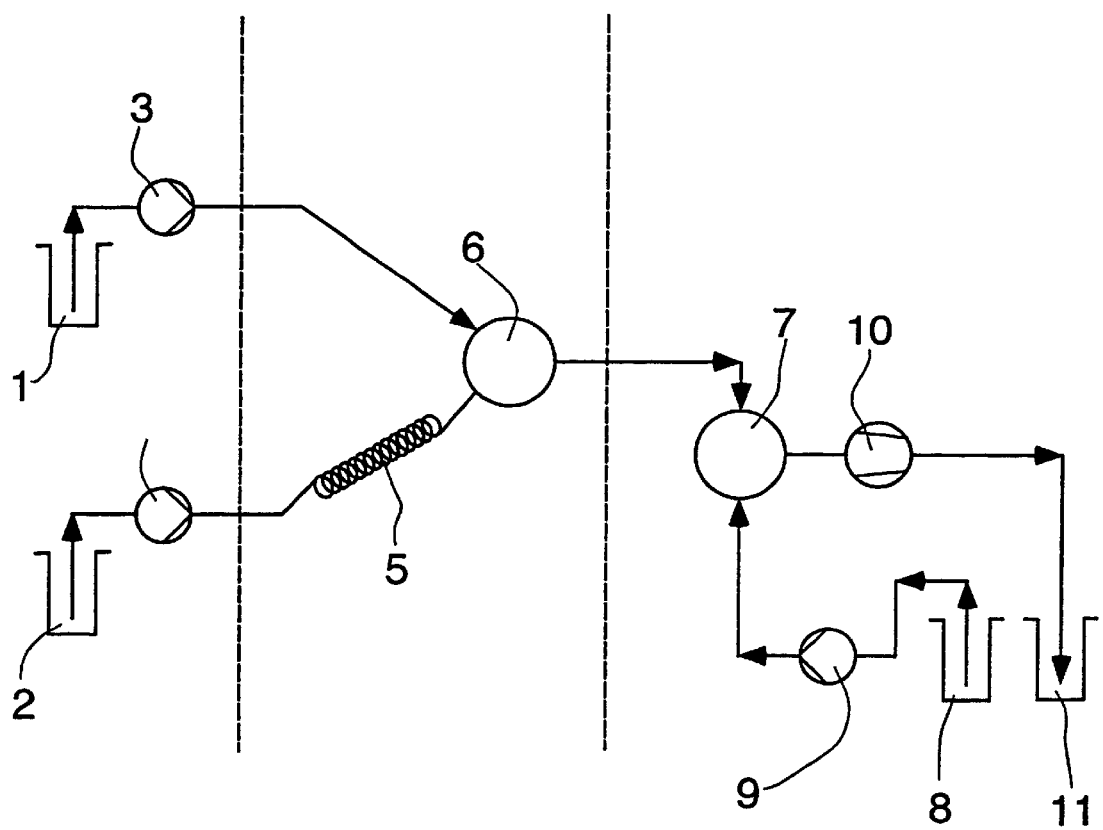
Figure 2:
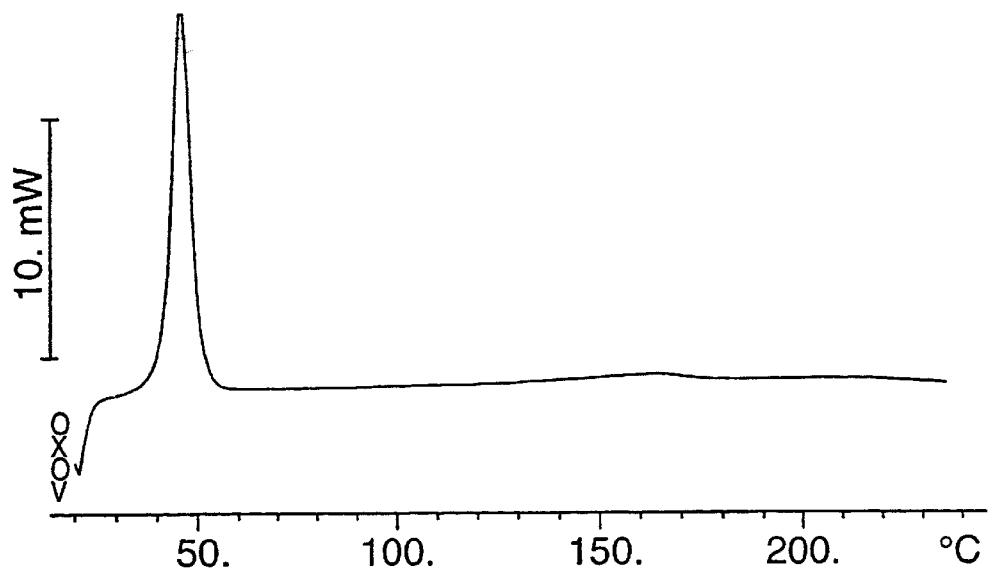
Figure 3:
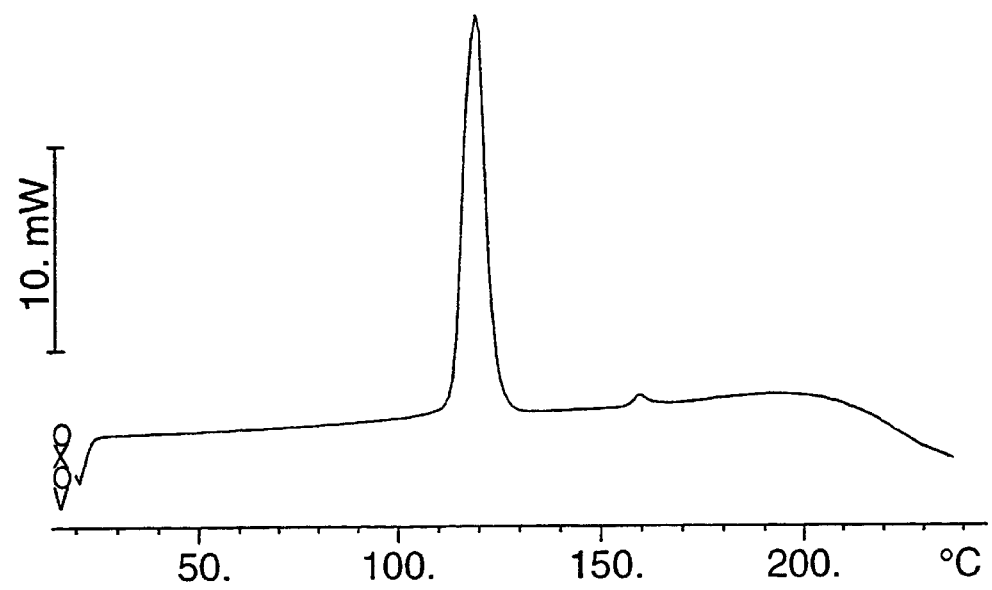
Figure 4:
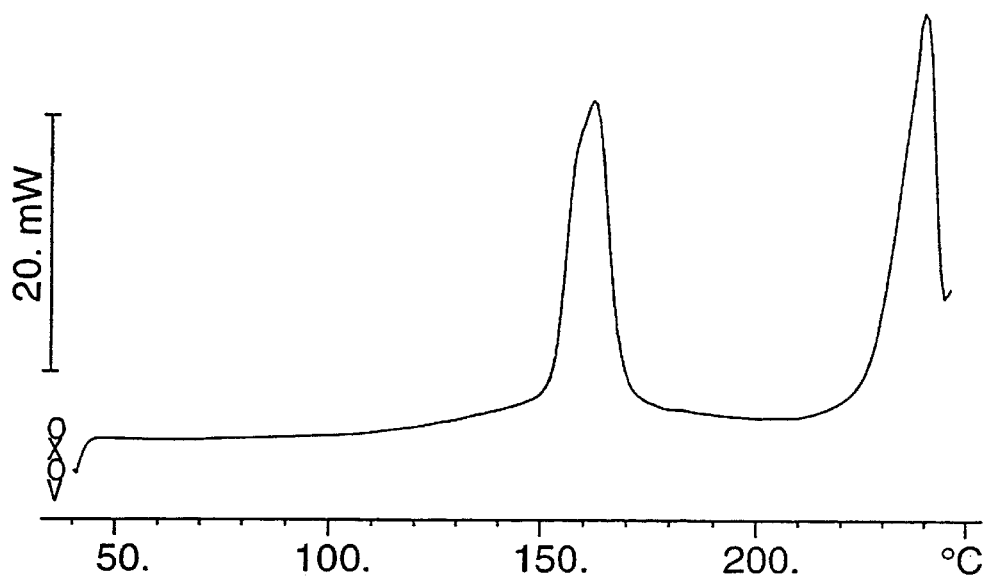
Figure 5:
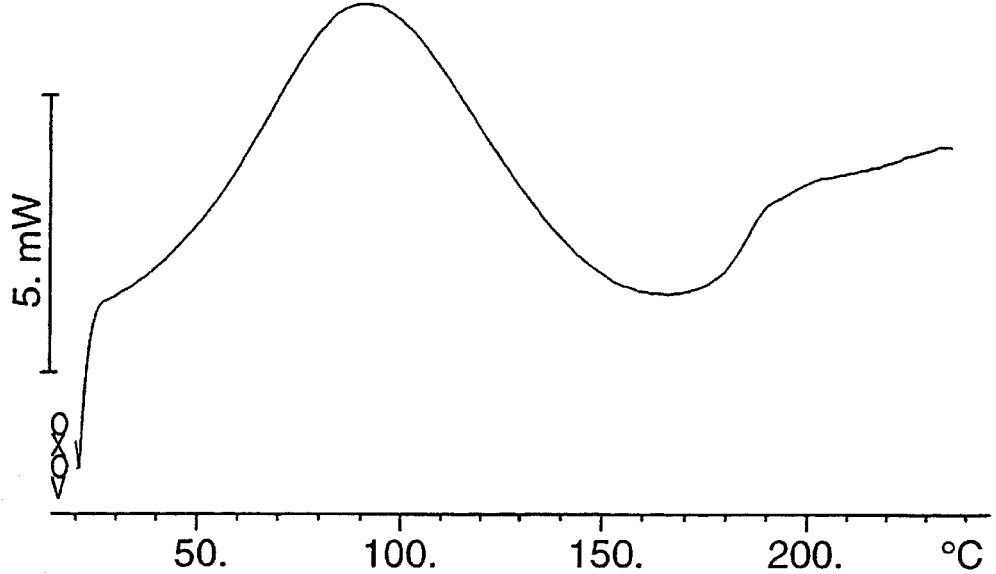
Figure 6:
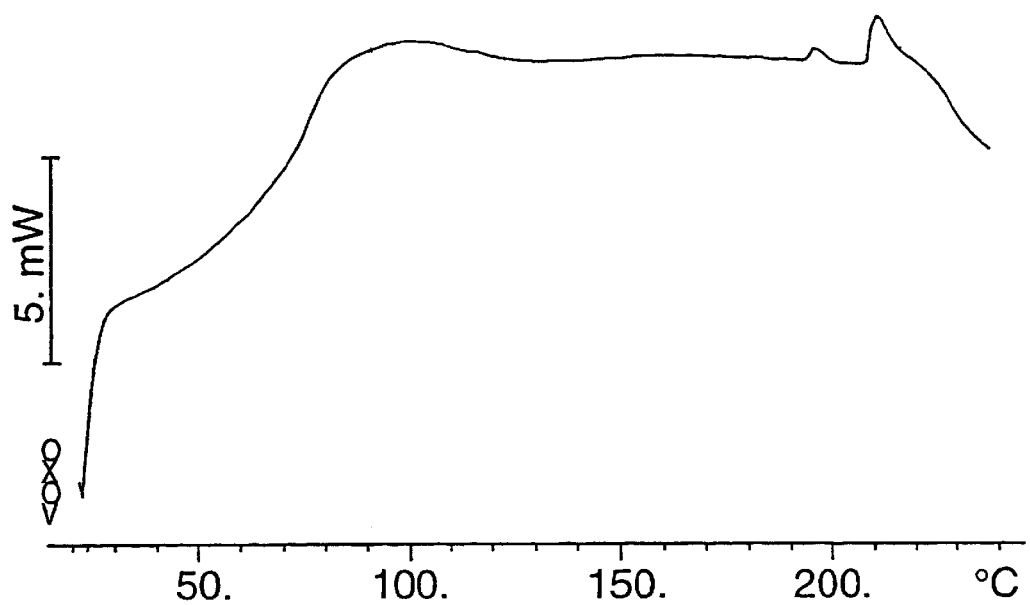
Figure 7:
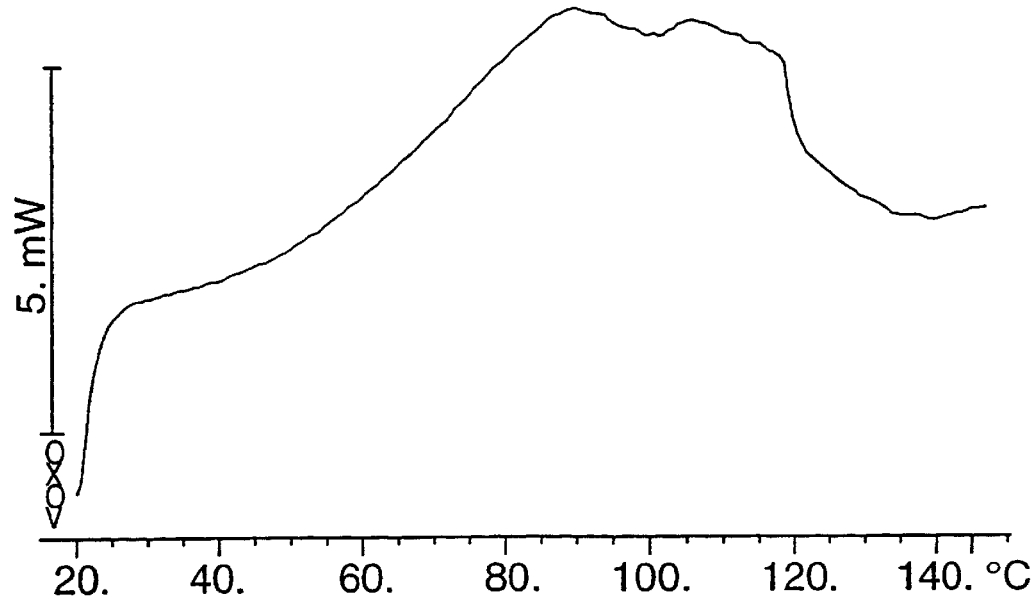
Figure 8:
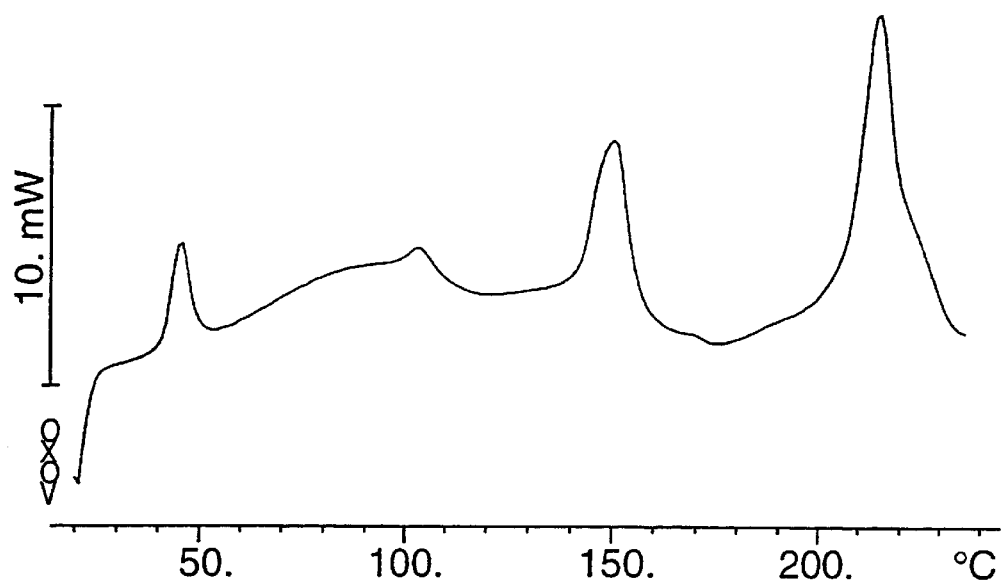
Figure 9:
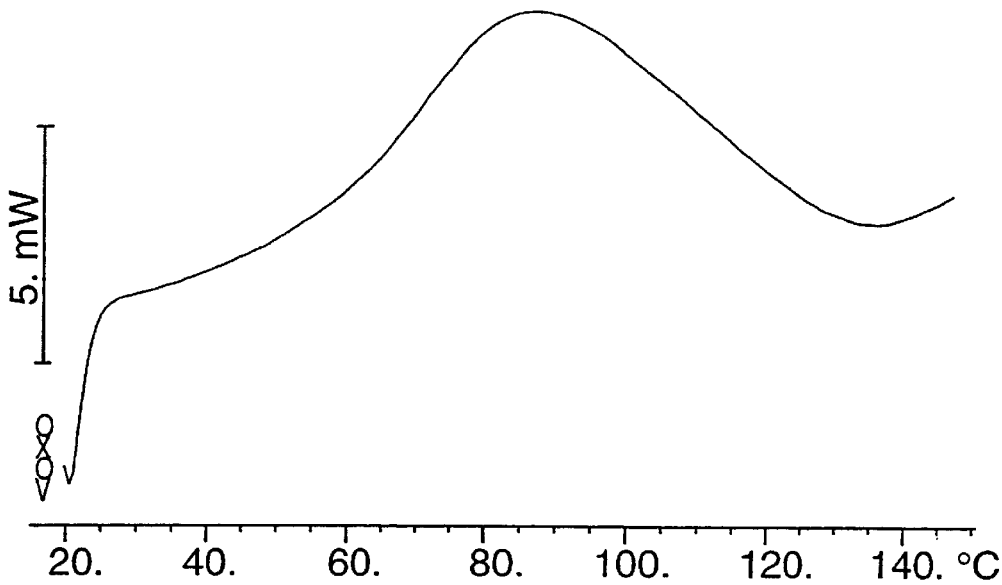
Figure 10:
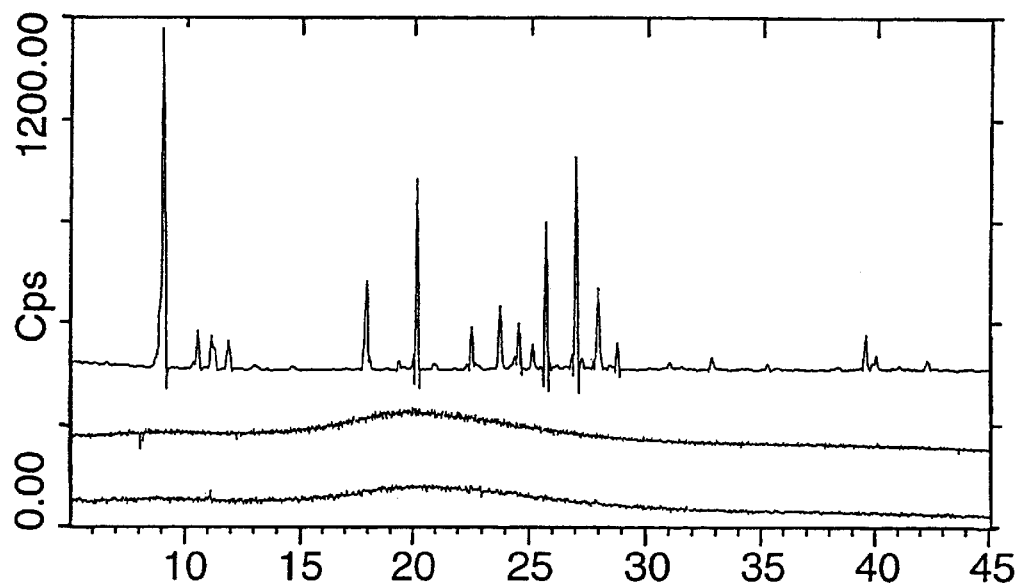

This Application is a 371 of PCT/EP97/05535 filed Oct. 8, 1997.

The present invention relates to solid crop protection compositions of one or more predominantly amorphous crop protection active ingredients which are solid per se and have solubility in water of less than 500 mg/l at 25° C. and of a coating enclosing these active ingredients.

The invention furthermore relates to methods of controlling undesirable vegetation, for controlling harmful plants and pests, and for regulating the growth of plants using the compositions according to the invention, and to a process for the preparation of the compositions according to the invention.

The starting materials for the preparation of suspensions of crop protection active ingredients which are solid per se are frequently solid—for example pulverulent or granular—formulations of the crop protection active ingredients, which are mixed with a suitable solvent, especially water. The crop protection active ingredients are predominantly in crystalline form in the solid formulations conventionally used for this purpose.

EP-A 65 193 discloses a process for coating carotenoids in which the carotenoid is dissolved, the carotenoid is precipitated in colloidal-disperse form from this solution by rapidly mixing it with an aqueous solution of a swellable colloid, and the resulting dispersion is freed from solvent and dispersant in a manner known per se.

U.S. Pat. No. 5,133,908 discloses using nanoparticles—i.e. particles with an average diameter in the nanometer range—as carriers for active ingredients and, if appropriate, drying them by means of lyophilization. Preparation is effected in a process at low temperature, low pressure and little or no stirring. As regards their stability and their properties upon use, these known products are as yet unsatisfactory in the crop protection sector.

It is an object of the present invention to provide a nanoparticulate formulation for solid crop protection active ingredients which is better suited to the preparation of liquid formulations which can be used in crop protection and which, in particular, leads to an enhanced efficacy of the crop protection active ingredients thus formulated.

The following must be mentioned as product characteristics in need of improvement:

the dissolution rate and the solubility of the compositions in the agriculturally important solvents, reduced application rates of crop protection active ingredients, prolonged duration of action of the formulated crop protection active ingredients, more potent initial action of the formulated crop protection active ingredient.

We have found that this object is achieved by the compositions defined at the outset.

There have furthermore been found the methods defined at the outset in which these compositions are used.

Suitable crop protection active ingredients for the purposes of the present invention are preferably those crop protection active ingredients or mixtures of these whose solubility in water is less than 100, in particular less than 10 mg/l, in each case at a temperature of 25° C.

The crop protection active ingredients may act not only against harmful fungi and pests in agriculture and the protection of timber, but also against undesired vegetation, or they may have growth-regulatory properties.

Suitable are, specifically, the following crop protection active ingredients or mixtures of these (whose nomenclature corresponds to that in "The Pesticide Manual", The British Crop Protection Council, 10th Edition, London, unless the efficient chemical nomenclature was used):

Fungicides:

dithiocarbamates and their derivatives, such as iron(III) dimethyldithiocarbamate, zinc bisdimethyldithiocarbamate, zinc ethylenebisdithiocarbamate, manganese ethylenebisdithiocarbamate, manganese zinc ethylenebisdithiocarbamate, tetramethylthiuram disulfide, zinc ethylenebisdithiocarbamate polymer, ammonia complex of zinc (N,N-ethylenebisdithiocarbamate), ammonia complex of zinc (N,N'-propylenebisdithiocarbamate), zinc (N,N'-propylenebisdithiocarbamate) polymer, N,N'-polypropylenebis(thiocarbamoyl)disulfide;

nitro derivatives, such as dinitro(1-methylheptyl)phenyl crotonate, 2-sec-butyl-4,6-dinitrophenyl-3,3-dimethyl acrylate, di-isopropyl 5-nitroisophthalate;

heterocyclic substances such as 2,4-dichloro-6-(o-chloranilino)-s-triazine, 2,3-dicyano-1,4-dithioanthraquinone, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthio-tetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 8-hydroxyquinoline and its copper salt, 2,3-dihydro-5-carboxanilido-6-methyl-1,4-oxathiine, 2-methylfuran-3-carboxanilide, 2-methylbenzanilide, N-formyl-N-morpholine-2,2,2-trichloroethyl acetal, piperazine-1,4-diylbis(2,2,2-trichloroethyl)formamide, 2,6-dimethyl-N-tridecyl-morpholine and its salts, 2,6-dimethyl-N-cyclododecyl-morpholine and its salts, N-[3-(p-tert-butylphenyl)-2-methylpropyl]-cis-2,6-dimethyl-morpholine, 1-[2-(2,4-dichlorophenyl)-4-n-propyl-1,3-dioxolan-2-ylmethyl]-1H-1,2,4-triazole, N-(n-propyl)-N-(2,4,6-trichloro-phenoxyethyl)-N'-imidazolylurea, 1-(4-chlorophenoxy)-3,3-dimethyl-1-(1H-1,2,4-triazol-1-yl)-2-butanone, (2-chlorophenyl)-(4-chlorophenyl)-5-pyrimidinemethanol, bis-(p-chlorophenyl)-3-pyridinemethanol, 1,2-bis(3-ethoxycarbonyl-2-thioureido)benzene, 1,2-bis(3-methoxycarbonyl-2-thioureido)benzene, [2-(4-chlorophenyl)ethyl]-(1,1-dimethylethyl)-1H-1,2,4-triazol-1-ethanol, and a variety of fungicides, such as 3-[3-(3,5-dimethyl-2-oxycyclohexyl)-2-hydroxyethyl)]glutarimide, hexachlorobenzene, methyl N-(2,6-dimethylphenyl)-N-(2-furoyl)-DL-alaninate, N-(2,6-dimethylphenyl)-N-chloracetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-1-isopropylcarbamoylhydantoin, N-(3,5-dichlorophenyl)-1,2-dimethylcyclopropane-1,2-dicarboximide, 1-[2-(2,4-dichlorophenyl)pentyl]-1H-1,2,4-triazole, 2,4-difluoro-α-(1H-1,2,4-triazolyl-1-methyl)benzhydryl alcohol, 1-((bis-(4-fluorophenyl)methylsilyl)methyl)-1H-1,2,4-triazole, strobilurins such as methyl E-methoximino-[a-(o-tolyloxy)-o-tolyl]-acetate, methyl E-2-{2-[6-(2- cyanophenoxy)-pyrimidin-4-yloxy]-phenyl}-3-methoxyacrylate, N-methyl E-methoximino-[α-(2-phenoxyphenyl)]-acetamide, N-methyl E-methoximino-[α-(2,5-dimethylphenoxy)-o-tolyl]-acetamide, anilinopyrimidines such as N-(4,6-dimethylpyrimidin-2-yl)aniline, N-[4-methyl-6-(1-propinyl)pyrimidin-2-yl]aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine, (+)-cis-1-(4-chlorophenyl)-2-(1H-1,2,4-triazol-1-yl)cyclo-heptanol, methyl (E)-2-{2-[6-(2-cyanophenoxy)pyrimidin-4-yloxy]phenyl}-3-methoxyacrylate and in particular the azol active ingredients N-propyl-N-[2,4,6-trichlorophenoxy)ethyl]imidazole-1-carboxamide (prochloraz), (Z)-2-(1,2,4-triazol-1-ylmethyl)-2-(4-fluorophenyl)-3-(2-chlorophenyl)oxirane (epoxiconazole), 1-butyl-1-(2,4-dichlorophenyl)-2-(1,2,4-triazol-1-yl)ethanol (hexaconazol), 1-[(2-chlorophenyl)methyl]-1-(1,1-dimethyl)-2-(1,2,4-triazol-1-yl-ethanol, 1-(4-fluorophenyl)-1-(2-fluorophenyl)-2-(1,2,4-triazol-1-yl)ethanol (flutriafol), (RS)-4-(4-chlorophenyl)-2-phenyl-2-(1H-1,2,4-triazol-1-ylmethyl)-butyronitrile, 1-[(2RS,4RS; 2RS,4SR)-4-bromo-2-(2,4-dichlorophenyl)tetrahydrofurfuryl]-1H-1,2,4-triazole, (RS)-2,2-dimethyl-3-(2-chlorobenzyl)-4-(1H-1,2,4-triazol-1-yl)butan-3-ol, bitertanol, triadimefon, triadimenol, bromuconazole, cyproconazole, difenoconazole, diniconazole, imibenconazole, propiconazole, flusilazole, tebuconazole, imazalil, penconazole, tetraconazole, metconazole, fluquinconazole, fenbuconazole, triticonazole.

Preferred azol active ingredients are prochloraz, epoxiconazole, hexaconazole, cyproconazole, difenoconazole, propiconazole, flusilazole, diniconazole, triticonazole and tebuconazole, the use of epoxiconazole being especially advantageous.

The active ingredients may also exist in the form of the salts or metal complexes thereof. These mixtures are also covered by the invention.

The salts are prepared by reaction with acids, for example hydrohalic acids such as hydrofluoric acid, hydrochloric acid, hydrobromic acid or hydroiodic acid or sulfuric acid, phosphoric acid, nitric acid or organic acids such as acetic acid, trifluoroacetic acid, trichloroacetic acid, propionic acid, glycolic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid or 1,2-naphthalenedisulfonic acid.

Metal complexes may comprise only a component (a) or a component (b) or else several components (a) or (b), as desired. It is also possible to prepare metal complexes which comprise both components (a) and (b) jointly in the form of a mixed complex.

Metal complexes are prepared from the basic organic molecule and an inorganic or organic metal salt, for example the halides, nitrates, sulfates, phosphates, acetates, trifluoroacetates, trichloroacetates, propionates, tartrates, sulfonates, salicylates or benzoates of the metals of the second Main Group such as calcium and magnesium and the third and fourth Main Groups such as aluminum, tin or lead, and the first through to the eighth Subgroup such as chromium, manganese, iron, cobalt, nickel, copper and zinc.

Preferred are the Subgroup elements of the 4th Period, in particular copper. The metals can exist in the various balance stages which they can assume. The metal complexes may comprise one or more organic moieties as ligands.

Herbicidal active ingredients which may be mentioned are:

thiadiazoles:
  bromobutide, dimepiperate, diphenamid, etobenzanid (benzchlomet), flamprop-methyl, isoxaben, naptalame, pronamid (propyzamid), propanil, anilides:
  anilofos, mefenacet
  2,4-D, 2,4-DB, clomeprop, dichlorprop, dichlorprop-P, fluroxypyr, MCPB, napropamide, napropanilide, triclopyr, bleaches:
  diflufenican, fluorochloridone, flupoxam, fluridone, pyrazolate, sulcotrione (chlormesulone), carbamates:
  butylate, chlorpropham, cycloate, desmedipham, EPTC, esprocarb, molinate, orbencarb, pebulate, phenmedipham, propham, prosulfocarb, pyributicarb, thiobencarb (benthiocarb), thiocarbazil, triallate, vernolate, quinolinecarboxylic acids:
  quinclorac, quinmerac, chloracetanilides:
  acetochlor, alachlor, butachlor, butenachlor, metazachlor, metolachlor, pretilachlor, thenylchlor, cyclohexenones:
  alloxydim, clethodim, cycloxydim, sethoxydim, tralkoxydim, dihydrobenzofuran:
  ethofumesate, dihydrofuran-3-one:
  flurtamone, dinitroanilines:
  benefin, butralin, dinitramin, ethalfluralin, fluchloralin, oryzalin, pendimethalin, prodiamine, trifluralin, dinitrophenols:
  bromofenoxim, dinoterb, DNOC, diphenyl ethers:
  acifluorfen-sodium, aclonifen, bifenox, chlornitrofen (CNP), ethoxyfen, fluoroglycofen-ethyl, fomesafen, lactofen, oxyfluorfen, urea:
  chlorbromuron, chlortoluron, cumyluron, dibenzyluron, dimefuron, diuron, dymron, fluometuron, isoproturon, linuron, methabenzthiazuron, metobenzuron, neburon, siduron, imidazolinones:
  imazaquin, oxadiazoles:
  oxadiargyl, oxadiazon, oxirane:
  tridiphane, phenols:
  bromoxynil, ioxynil phenoxyphenoxypropionic esters:
  clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl phenylpropionic acid:
    chlorophenprop-methyl,
ppi:
    benzofenap, flumiclorac-pentyl, sulfentrazone,
pyridazines:
    chloridazon, norflurazon, pyridate,
pyridinecarboxylic acids:
    dithiopyr, picloram, thiazopyr,
pyrimidyl ethers:
    pyrithiobac-acid, KIH-6127,
sulfonamides:
    flumetsulam, metosulam,
sulfonylureas:
    amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, primisulfuron, prosulfuron, pyrazosulfuron-ethyl, rimsulfuron, sulfometuron-methyl, thifensulfuron-methyl, triasulfuron, triflusulfuron-methyl,
triazines:
    ametryn, atrazine, cyanazine, dimethamethryn, prometryn, propazine, simazine, simetryn, terbumeton, terbutryn, terbutylazine, trietazine,
triazolcarboxamide:
    triazofenamide,
uracil:
    lenacil,
various:
    benazolin, benfuresate, bensulide, butamifos, chlorthal-dimethyl (DCPA), cinmethylin, dichlobenil, fluorbentranil, mefluidide, piperophos.

Suitable insecticidal and acaricidal crop protection active ingredients are:
    cyanophosphates such as sulprofos, chlorpyrifos, phosalone, pirimiphos-methyl, fenitrothion, phosmet, azinophos-methyl, profenofos and methidathion; carbamates such as carbosulfan, fenoxycarb, thiocarb and carbaryl; pyrethroids such as deltamethrin, ethofenprox, fluvalinate, esfenvalerate, beta-cyfluthrin, cypermethrin, lambda-cyhalothrin, cycloprothrin, bifenthin, tralomethrin; other insecticides such as chlorfenapyr, amitraz, endosulfan, bensulfap, fipronil and pyridafenthion; juvenoids such as flucycloxuron, teflubenzuron, hexaflumuron, lufenuron, diflubenzuron, tebufenozide and fenoxycarb; acaricides such as fenbutatin-oxide, pyridaben, fenpyroximate, fenazaquin, dicofol, cyhexatin and tebufenpyrad.

Preferred crop protection active ingredients are BAS 480 F (common name: epoxiconazol), BAS 490 F (common name: kresoxim-methyl), chloridazon and N-(((4-methoxy-6-[trifluoromethyl]-1,3,5-triazin-2-yl)amino)-carbonyl)-2-(trifluoromethyl)benzenesulfonamide.

Expecially preferred crop protection active ingredients are N-(1-ethylpropyl)-3,4-dimethyl-2,6-dinitroaniline (pendimethalin) and chlorpyrifos.

Several crop protection active ingredients, including active ingredients for different indications, may be present alongside each other in the compositions according to the invention.

When preparing the compositions, the crop protection active ingredient is preferably either employed as such or else it may be liberated from one of its salts or, preferably, employed as such.

As a rule, the crop protection active ingredients used have a purity of 90 to 100, preferably 95 to 100% (according to NMR spectrum).

The abovementioned crop protection active ingredients are present in the compositions according to the invention in a predominantly amorphous state. "Predominantly amorphous" means that over half, preferably over 70%, of the crop protection active ingredient in the compositions according to the invention, are X-amorphous, as can be demonstrated by X-ray structure analysis.

Conversely, the degree of crystallinity of the crop protection active ingredients in the compositions according to the invention can be determined reliably with methods known per se, such as X-ray wide-angle diffraction (cf. H. P. Klug, L. E. Alexander, "X-Ray Diffraction Procedures for Polycrystalline and Amorphous Materials", John Wiley, New York, 1959) or by means of Differential Scanning Calorimetry (DSC) (cf. P. J. Haines, "Thermal Methods of Analysis", Blackie Academic & Professional, Chapman & Hall, London, 1995).

Additional formulation additives which are customary in crop protection and which do not increase the solubility of the crop protection active ingredient beyond a value of 500 mg/l or which trigger or promote crystallization of the predominantly amorphous crop protection active ingredient may also be added to the crop protection active ingredients.

Suitable customary formulation additives are especially stabilizers and plasticizers.

In general, the stabilizers have one or more of the following tasks, depending on the individual case:
    stabilization of the amorphous state of the crop protection active ingredients in the compositions according to the invention,
    preventing the crystalline growth of the particles of crop protection active ingredients dispersed in a liquid medium at the expense of other particles, which may result in undesired sedimentation of the enlarged particles, and
    controlling the size of particles generated.

Suitable stabilizers are, equally, low-molecular-weight substances and polymeric substances and mixtures of these.

Preferred low-molecular-weight stabilizers are mono- and diglycerides, esters of monoglycerides with acetic acid, citric acid, lactic acid or diacetyltartaric acid, alkylglucosides, sorbitane fatty esters, propylene glycol fatty esters, stearoyl-2-lactylate, lecithine, fatty acid derivatives of ureas and urethanes such as dioleylurea and N-oleyloleylurethane. Particularly suitable are ascorbyl palmitate and fatty acid carbonates such as dioleyl carbonate.

Preferred polymeric stabilizers are polyglycerol fatty acid esters and homo- and copolymers based on the following monomers: ethylene oxide, propylene oxide, acrylic acid, maleic anhydride, methyl acrylate, ethyl acrylate, tert-butyl acrylate, methacrylic acid, styrene, isobutene, lactic acid, N-vinyl-2-pyrrolidone, vinyl acetate, vinyl acrylate, α-aspartic acid and β-aspartic acid.

Particularly preferred polymeric stabilizers are:
    homopolymers of vinylpyrrolidone, acrylic acid or lactic acid and
    copolymers of styrene and acrylic acid; acrylic acid and methacrylic acid; vinyl acrylate and vinyl acetate; α- and β-aspartic acid; vinylpyrrolid-2-one and vinyl acetate; methyl acrylate; ethyl acrylate and tert-butyl acrylate; ethylene oxide and propylene oxide; isobutene and maleic anhydride.

Very specially preferred polymeric stabilizers are styrene/acrylic acid copolymers of 40 to 80 mol % styrene and 60 to 20 mol % acrylic acid, in particular 50 to 70 mol % styrene and 50 to 30 mol % acrylic acid.

In general, the stabilizers amount to 0 to 30 and, in particular, 0 to 10, % by weight of the compositions according to the invention, based on the solids content of the crop protection compositions according to the invention.

The plasticizers almost exclusively form part of the coating of the compositions according to the invention.

The function of the plasticizers is, in particular, to improve the mechanical properties of the compositions according to the invention. Examples of suitable plasticizers are sugars or sugar alcohols such as sucrose, glucose, lactose, invert sugar, sorbitol, mannitol or glycerol.

Normally, the plasticizers amount to 0 to 70% by weight of the compositions according to the invention, based on the solids content of the crop protection compositions according to the invention.

As a rule, the abovementioned other formulation additives, in total, amount to 20 to 80% by weight of the compositions according to the invention, which, naturally, depends on the crop protection active ingredient in question.

When, later, the compositions are used in crop protection for the preparation of spray mixtures, the purpose of the coating is mainly to stabilize the coated particles in the spray mixture against agglomeration and thus to suppress sedimentation.

Presumably, the explanation of this effect is that the coating leads to the same kind of electric charge, or, when using a crop protection active ingredient in the form of a salt, an increase in charge or charge reversal of the particles. The particles, which now have the same kind of electric charge, repel each other (electrostatic stabilization), that the coated particles are kept spatially apart from each other(sterical stabilization) and/or
- that the coating continues to slow down or suppress further growth of the particles by means of Ostwald ripening (cf. T. F. Tadros, "Surfactants in Agrochemicals", Surfactant Science Series, Volume 54, Marcel Dekker, New York, 1995).

Materials which are suitable for the coating are boundary- or surface-active polymeric colloids or amphiphilic, optionally oligomeric, compounds of this type, or mixtures of these.

Polymeric colloids of this type which are preferably used for the coating are biopolymers and modified biopolymers such as gelatin from pigs, cattle or fish, for example gelatin B 100 Bloom (Stoess, Eberbach, Germany) and Gelita Sol® P (Stoess, ibid.), pectin, chitosan, starch, dextrin, gum arabic, casein, caseinate, methylcellulose, carboxymethylcellulose, hydroxypropylcellulose, alginates and lignin derivatives such as lignosulfonate.

Also suitable are synthetic anionic, cationic and neutral polymers such as polyvinyl alcohol, polyvinylpyrrolidone, polyacrylic acid, polycarboxylates, polyethylene glycols, maleic anhydride/isobutene copolymers, vinylpyrrolidone/vinyl acetate copolymers, naphthalenesulfonic acid condensates (for example CAS No. 9017-33-8, 9069-80-1, 9084-06-4, 9008-63-3, 108171-28-4, 86352-09-2) and phenolsulfonic acid condensates (for example CAS No. 52277-29-9, 102980-04-1) and polyethylenimine, polyvinylamine, polyvinylformamide and partially hydrolyzed polyvinylformamide.

Preferred amphiphilic compounds which are suitable as coating materials are the following surfactants or, preferably, mixtures of these, in which the alkyl chains may be linear or branched and which have alkyl chains of in general between 8 and 20 carbon atoms:

1. Anionic surfactants
   - soaps (alkali metal/alkaline earth metal/ammonium salts of the fatty acids), for example potassium stearate
   - alkyl sulfates
   - alkyl ether sulfates
   - alkyl/isoalkylsulfonates
   - alkylbenzenesulfonates, for example sodium dodecylbenzene sulfonate
   - alkylnaphthalenesulfonate
   - alkylmethyl ester sulfonates
   - acyl glutamates
   - alkylsuccinic ester sulfonates
   - alkyl mono/diphosphates
   - sarcosinates, for example sodium lauroylsarcosinate
   - taurates
2. Cationic surfactants
   - alkyltrimethylammonium halides/alkylsulfates
   - alkylpyridinium halides
   - dialkyldimethylammonium halides/alkylsulfates
3. Nonionic surfactants
   - alkoxylated animal/vegetable fats and oils, for example corn oil ethoxylates, castor oil ethoxylates, tallow fat ethoxylates
   - glycerol esters, for example glycerol monostearate
   - fatty alcohol alkoxylates and oxoalcohol alkoxylates
   - fatty acid alkoxylates, for example oleic acid ethoxylates
   - alkylphenol alkoxylates, for example isononylphenol ethoxylates
   - fatty amine alkoxylates
   - fatty acid amide alkoxylates
   - sugar surfactants, for example sorbitan fatty acid esters (sorbitan monooleate, sorbitan tristearate), polyoxyethylene sorbitan fatty acid esters, alkyl polyglycosides, N-alkylgluconamides
   - alkylmethyl sulfoxides
   - alkyldimethylphosphine oxides, for example tetradecyldimethylphosphine oxide
4. Zwitterionic surfactants
   - sulfobetaines
   - carboxybetaines
   - alkyldimethylamine oxides, for example tetradecyldimethylamine oxide
5. Polymer surfactants
   - di- tri- and multi-block polymers of the (AB)x-, ABA and BAB type, for example polyethylene oxide-block-polypropylene oxide, polystyrene-block-polyethylene oxide
   - AB comb polymers, for example polymeth/acrylate-comb-polyethylene oxide
6. Others
   - perfluorinated surfactants
   - silicone surfactants
   - phospholipids, for example lecithin
   - amino acid surfactants, for example N-lauroylglutamate.

Typically, the compositions according to the invention are composed as follows:

0.5–75% by weight crop protection active ingredient
0–30% by weight stabilizer
0–70% by weight plasticizer
10–70% by weight coating material Preferred are compositions which are composed as follows:

5–50% by weight crop protection active ingredient
0–20% by weight stabilizer
20–70% by weight plasticizer
10–60% by weight coating material Especially preferred are compositions which are composed as follows:
10–40% by weight crop protection active ingredient
0–10% by weight stabilizer
20–50% by weight plasticizer
10–50% by weight coating material The composition according to the invention is prepared in such a way that a liquid formulation of the crop protection active ingredient is mixed with a liquid formulation of a coating material and the resulting coated crop protection active ingredient is dried to a high degree in a manner known per se.

The crop protection active ingredient or its salt is converted into a liquid formulation with the aid of a solvent. "Solvents" are to be understood as meaning water, organic solvents which are miscible with water, mixtures of water and the organic solvents, and mixtures of the organic solvents. As a rule, the liquid product which can thus be obtained is a molecular-disperse solution of the crop protection active ingredient.

Suitable organic solvents which are miscible with water are those which are volatile and thermostable and which only contain carbon, hydrogen and oxygen. They are expediently miscible with water to at least 10% and have a boiling point of below 200° C. and/or have less than 10 carbon atoms. Preferred are alkohols, ethers, esters, ketones and acetals of this type. Substances which are used in particular are ethanol, n-propanol, isopropanol, 1,2-butanediol 1-methyl ether, 1,2-propanediol-1-n-propyl ether or acetone.

In a preferred embodiment of the process according to the invention, the molecular-disperse solution of the crop protection active ingredient is prepared in such a way that the active ingredient is first dissolved in the—if desired previously heated—organic solvents which are miscible with water, if appropriate under pressure.

The turbulent mixing of the molecular-disperse solution of the crop protection active ingredient with the liquid formulation of the coating material (termed "dispersing solution") converts the former into a colloid-stable dispersion (micronizate) of coated particles of the essentially amorphous crop protection active ingredient.

The coating material normally amounts to 0.5 to 10, and preferably 1 to 5, % by weight of the dispersing solution. As a rule, 0.1 to 10 times the amount of coating material is employed, based on the weight of the crop protection active ingredient.

A preferred embodiment of the process according to the invention is that there is always an excess of the coating material in the dispersing solution.

To achieve particles as small as possible upon mixing, it is expedient to produce a vigorous turbulence in the mixing chamber by stirring or shaking the active ingredient solution and the dispersing solution with mechanical aids or, in particular, by injecting a forced stream of these two components into a mixing chamber.

FIG. 1 shows a suitable arrangement with mixing chamber.

A suspension of the crop protection active ingredient in the solvent of choice in concentration of 0.1 to 50% by weight based on the mixture, if appropriate with addition of 0.1 to 30% by weight of stabilizers, is introduced into container (1). Container (2) contains the solvent without admixture of the crop protection active ingredient. The active ingredient suspensions and the solvent are fed to the mixing chamber (6) via pumps (3) and (4), it being possible for the mixing ratio to be set by selecting the flow rate of each of the pumps, and it is chosen in such a way that an active ingredient concentration of 0.02 to 40% by weight based on the solution is formed in the mixing chamber, depending on solvent and residence time. The volume of the mixing chamber (6) is such that the residence time in (6) is preferably less than 10 seconds at the selected flow rate of pumps (3) and (4).

Before entering the mixing chamber, the solvent is brought to the desired temperature via the heat exchanger (5). Turbulent mixing in (6) causes the active ingredient to dissolve in the temperature range of 20 to 240° C., and the resulting solution enters the second mixing chamber (7) in which the active ingredient is precipitated in colloid-disperse form by admixing the dispersing solution via pump (9). The fine active ingredient dispersion leaves via the pressure control valve (10) and enters the storage container (11).

When setting the pressure control valve (10) to pressures above 1 bar, solvents may be used in the process at temperatures above their boiling point (under atmospheric pressure).

In the case of solvent-soluble crop protection active ingredients, it is possible that a molecular-disperse solution is formed as early as in the container (1). This solution may also be pumped directly into chamber (7).

As a rule, the process according to the invention gives a colloid-disperse liquid product which normally comprises 40 to 99.5, especially 60 to 95% by weight, of water and/or one or more water-miscible organic solvents.

As a rule, the average particle size in this colloid-disperse product is between 0.05 and 1.5, in most cases between 0.1 and 1, $\mu$m (measured by dynamic light scattering by the method of B. Chu, "Laser Light Scattering", Academic Press, New York, 1974). Depending on the boiling point, the solvents can be removed from the colloid-disperse intermediate in a manner known per se, for example by distillation, if appropriate under reduced pressure, or by extraction. Membrane filtration and freeze drying (lyophilization) are furthermore possible. However, the preferred method—if appropriate after concentration (falling-film evaporator)—is spray granulation, in particular spray drying and the twin-emulsion method.

The resulting dry powder normally comprises 1 to 1000, in most cases, however, 5 to 100 ppm of residual solvent. The residual water content is normally 0.01 to 10, in most cases 0.1 to 6, % by weight, based on the total mass of dry powder.

The presence of nanoparticle agglomerates in the dry powder depends mainly on the coating material and the drying conditions.

To promote the disintegration of such agglomerates upon dispersing the dry powder prior to use, the addition before drying of a spray adjuvant such as lactose or polyvinylpyrrolid-2-one to the colloid-disperse product after the mixing step is advantageous.

In a preferred embodiment of the process according to the invention, which is also especially advantageous per se, the active ingredient solution is prepared in the presence of one of the abovementioned stabilizers. Very particularly preferred in this context are ascorbyl palmitate and copolymers of acrylic acid and styrene.

When the dry powder thus obtainable is dispersed in water, it normally produces a finely disperse spray mixture with the crop protection active ingredients distributed in the form of nanoparticles, as before.

Besides, the skilled worker is familiar with further details of the process for the preparation of the dry powder, and no further explanation is therefore necessary (cf. EP-A 65 193 and EP-A 641 596).

The mean diameter of the redispersed nanoparticles (Hydrosol) is preferably 0.05 to 2, especially 0.05 to 1, in particular 0.1 to 0.8, $\mu$m.

The dry powder may reach the user in customary containers, especially bottles, cannisters or else bags made of chemical-resistant polymers. The use of water-soluble containers, amongst them especially water-soluble film bags, in particular those based on polyvinyl alcohol, is especially advantageous.

Prior to use, the compositions according to the invention are processed with water in a manner known per se by the practitioner, as a rule by the farmer, to give the ready-to-use spray mixtures.

The spray mixtures normally comprise 0.0001 to 20, preferably 0.001 to 10, in particular 0.01 to 1, % by weight, of the crop protection active ingredient.

The spray mixtures can be applied in a manner known per se, especially by spraying, such as using a mobile sprayer, making use of finely distributing nozzles. The equipment and management techniques also used for this purpose are known to those skilled in the art.

The following text will illustrate the application of compositions which comprise a herbicidal crop protection active ingredient. These explanations analogously also apply to crop protection active ingredients for other indications.

The active ingredient preparations according to the invention are suitable as herbicides and growth regulators.

As herbicides they effect very good control of undesired vegetation on non-crop areas, especially at high rates of application. In crops such as wheat, rice, maize, soya and cotton they act against broad-leaved weeds and grass weeds without damaging the crop plants substantially. This effect is observed especially at low rates of application.

Depending on the application method in question, the compositions can additionally be employed in a further number of crop plants for eliminating undesirable plants. Examples of suitable crops are the following:

*Allium cepa, Ananas comosus, Arachis hypogaea, Asparagus officinalis, Beta vulgaris* ssp. *altissima, Beta vulgaris* ssp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum* (*N.rustica*), *Olea europaea, Oryza sativa, Phaseolus lunatus, Phaseolus vulgaris, Picea abies,* Pinus spp., *Pisum sativum, Prunus avium, Prunus persica, Pyrus communis, Ribes sylestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera, Zea mays.*

Moreover the herbicidal compositions can also be used as herbicides in crops which tolerate the action of herbicides due to breeding including genetic engineering methods.

Examples of undesired plants are: cockspur grass (*Echinochloa crus-galli*), *Brachiaria plantaginea, Ischaemum rugosum, Leptochloa dubia,* redroot pigweed (*Amaranthus retroflexus*), common lamb's-quarters (*Chenopodium album*), catchweed bedstraw (*Galium aparine*), black nightshade (*Solanum nigrum*), blackgrass (*Alopecurus myosuroides*), wild oat (*Avena fatua*), smooth browngrass (*Bromus inermis*), annual bluegrass (*Poa annua*), giant foxtail (*Setaria faberii*), (volunteer) wheat (*Triticum aestivum*), (volunteer) corn (*Zea mays*).

The herbicidal compositions or the active ingredients can be applied pre- or post-emergence. If the active ingredients are less well tolerated by certain crop plants, application techniques may be used in which the herbicidal compositions are sprayed, with the aid of the spray apparatus, in such a way that they come into as little contact, if any, with the leaves of the sensitive crop plants while reaching the leaves of the undesirable plants which grow underneath, or the bare soil (post-directed, lay-by).

The herbicidal compositions can be employed, for example, in the form of directly sprayable aqueous suspensions, also highly-concentrated aqueous, oily or other suspensions, pastes, dusts, materials for spreading or granules, by means of spraying, atomizing, dusting, spreading or pouring. The use forms depend on the intended purposes; in any case, they should guarantee the finest possible distribution of the active ingredients according to the invention.

To widen the spectrum of action and to achieve synergistic effects, the herbicidal compositions according to the invention can be mixed and applied jointly with a large number of representatives of other groups of herbicidally active ingredients. Suitable components in mixtures are, for example, 1,2,4-thiadiazoles, 1,3,4-thiadiazoles, amides, aminophosphoric acid and its derivatives, aminotriazoles, anilides, (het)aryloxyalkanic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenylderivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compositions of the invention alone or in combination with other herbicides, in the form of a mixture with additional other crop protection compositions, for example with pesticides or agents for controlling phytopathogenic fungi or bacteria or with growth regulators. Also of interest are mixtures with mineral salt solutions which are employed for treating nutritional and trace element deficiencies. Nonphytotoxic oils and oil concentrates can also be added.

Moreover, the compositions according to the invention are capable of affecting the various developmental stages of a plant and can therefore be employed as growth regulators. The multiplicity of action of the plant growth regulators depends especially a) on the plant species and plant variety,
b) on the application timing based on the developmental stage of the plant, and on the season,
c) on the site and method of application (for example seed dressing, soil treatment, foliar application or, in the case of trees, injection into the stem),
d) on climatic factors (for example temperature, precipitation, in addition also day length and light intensity),
e) on the nature of the soil (including fertilization),
f) on formulation or use form of the active ingredient and
g) on the used concentrations of the active substance.

Amongst the series of the various applications which are possible for the plant growth regulators according to the invention in crop production, in agriculture and in horticulture, a few shall be mentioned hereinbelow:

A. The compositions which can be used according to the invention allow the vegetative growth of the plants to be inhibited greatly, which manifests itself in particular in a reduced longitudinal growth. Accordingly, the treated plants exhibit stunted growth; moreover, the color of the leaves is darker.

Advantageous for practice conditions is a reduced growth intensity of grasses on verges, hedges, canal banks, and on lawns such as amenity areas, turf and in orchards, on ornamental lawns and airports, so that grass cutting, which is labor-intensive and expensive, can be reduced.

Also of economic interest is increased standing power of crops which are prone to lodging, such as cereals, corn, sunflowers and soya. Stem shortening and stem strengthening, which are caused during this process, reduce or eliminate the danger of "lodging" (breaking) of plants under unfavorable weather conditions prior to harvesting.

Also important is the use of growth regulators for inhibiting the longitudinal growth and for altering in the course of time the maturation rate in cotton. This allows fully mechanical harvesting of this important crop plant.

In the case of fruit and other trees, pruning costs can be cut using growth regulators. Moreover, biennial bearing of fruit trees can be interrupted by growth regulators.

Also, the use of growth regulators can increase or inhibit lateral branching of the plants. This is of interest if, for example, the formation of axial shoots (suckers) is to be inhibited for the benefit of foliar growth.

Growth regulators also permit frost resistance to be considerably improved in the case of, for example, winter oilseed rape. On the one hand, this inhibits longitudinal growth and development of a lush leaf or plant biomass (which is therefore especially susceptible to frost). On the other hand, the vegetative developmental stage of the young oilseed rape plants is retained after sowing and before the winter frosts start, despite advantageous growth conditions. This also eliminates the danger of frost to those plants which tend to lose floral inhibition early and switch to the generative phase. In other crops too, for example in winter cereals, it is advantageous for the stands to tiller freely in autumn, but to overwinter without unduly lush growth, due to treatment with compounds according to the invention. A greater sensitivity to frost and—because the leaf or plant biomass is relatively low—attack by various diseases (for example fungal diseases) can thus be prevented. Moreover, inhibition of the vegetative growth allows denser planting in the soil in the case of many crop plants, so that a higher yield can be achieved based on the soil area.

B. The growth regulators permit higher yields of plant organs and of plant constituents to be achieved. Thus, for example, it is possible to induce the growth of more buds, flowers, leaves, fruits, seed kernels, roots and tubers, to increase the sugar content in sugar-beet, sugar-cane and citrus fruit, to increase the protein content in cereals or soya or to stimulate rubber trees to higher latex production.

The compositions according to the invention can cause higher yields by engaging in the plant metabolism or by promoting or inhibiting the vegetative and/or the generative growth.

C. Finally, plant growth regulators make possible shorter or extended development stages, and increased or delayed maturing of the harvested plant organs before or after harvesting.

Of economic interest, for example, is greater ease of harvesting, which is made possible by concentrating, in the course of time, the dehiscence, or reduced adherence to the tree, in the case of citrus fruit, olives or in other species and varieties of pome fruit, stone fruit and nuts. The same mechanism, i.e. promotion of the formation of abscission tissue between fruit, or leaf, and shoot of the plant is also essential for the readily controllable defoliation of useful plants such as, for example, cotton.

D. Furthermore, the water consumption of plants may be reduced by means of growth regulators. This is particularly important for farmed areas which must be irrigated artificially, which leads to high costs, for example in arid or semi-arid regions. The use of the substances according to the invention allows the irrigation intensity to be reduced, which means more economical management. The effect of growth regulators means better utilization of the available water since, inter alia, stomatal opening is reduced,
a thicker epidermis and cuticula are formed,
root penetration of the soil is improved and
the microclimate within the plant stand is favorably affected by more compact growth.

The compositions are especially suitable for shortening the stalk of crop plants such as barley, oilseed rape and wheat.

The growth regulators prepared in accordance with the invention can be provided to the crop plants both via the seed (in the form of a seed treatment) and via the soil, i.e. via the root and—especially preferably—by foliar spray treatment. The preparation of the compositions is similar to the preparation of herbicides (see above).

The application rate of growth-regulatory active ingredient is not critical due to the high plant tolerance. The optimum application rate depends on the intended aim, the season, the target plants and the growth stages.

EXAMPLES

Preparation Examples

Analyses

| | |
|---|---|
| DSC: | Mettler TA4000 apparatus, heating rate 10° C./min |
| Quasi-elastic light scattering: | BI 90 apparatus by Brookhaven |
| Fraunhofer diffraction: | Particle Sizer 2600 apparatus by Malvern |
| X-ray wide-angle scattering: | Siemens D 5000 apparatus |

Preparation Example 1

Preparation of a dry powder, for example chlorpyrifos (active ingredient content: approx. 15% by weight)

a) Preparation of the Micronizate 24 g of chlorpyrifos (purity: 96.5% by weight) were stirred at 25° C. into a solution of 4.8 g ascorbyl palmitate in 146 g of 45 acetone, giving a clear solution. This solution was mixed with 113 g of acetone in the mixing chamber (6) at 163° C.

The chlorpyrifos was precipitated in colloid-disperse form in such a way that, after a residence time of 3.2 seconds, the molecular disperse solution was fed into the mixing chamber (7). There, the material was mixed at 34° C. with 3200 g of an aqueous solution, brought to pH 9.2 using 1 N NaOH, of 13.6 g of gelatin B 100 Bloom, 58.4 g of Gelita Sol® P and 48 g of lactose in fully demineralized water. During the entire process, the pressure was limited to 30 bar by means of a valve (10) to prevent evaporation of the solvent. A white, cloudy colloid-disperse chlorpyrifos dispersion was obtained in the receiving vessel (11).

The mean particle size was determined as 247 nm by quasi-elastic light scattering, the distribution range being ±37%. The mean of the volume distribution was determined by Fraunhofer diffraction as D(4,3)=0.62 µm, and the fines in the distribution were determined as 99.8%<1.22 µm.

b) Drying of the Dispersion from (a) to a Nanoparticulate Dry Powder

Spray drying of the product from Preparation Example 1 a) gave a free-flowing nanoparticulate dry powder. The active ingredient content in the powder was determined by chromatography as 15.42% by weight chlorpyrifos (in theory: 15.56% by weight). The dry powder dissolved in drinking water giving a white, cloudy dispersion (Hydrosol).

The mean particle size was determined immediately after redispersion by quasi-elastic light scattering as 333 nm at a distribution range of ±38%. The mean of the volume distribution was determined by Fraunhofer diffraction as D(4,3)=0.87 μm, and the fines in the distribution were determined as 87.8%<1.22 μm. No noticeable increase in particle size was observed in the course of 4–6 hours (cf. Table 1). The decrease in particle size observed within the first hour after redispersion reflects the disintegration and complete redispersion in the form of nanoparticles of the particle associations formed upon spray drying.

TABLE 1

Particle sizes (Fraunhofer diffraction) of a chlorpyrifos hydrosol comprising 0.2% of active ingredient, prepared by manually stirring the chlorpyrifos dry powder of b) into drinking water at room temperature on the day of spray drying.

| Time after redispersion Immediately | D (4,3) [μm] 0.87 | Fines <1.22 μm 87.8 |
|---|---|---|
| 1 h | 0.63 | 99.2 |
| 2 h | 0.63 | 98.7 |
| 3 h | 0.65 | 97.1 |
| 4 h | 0.64 | 97.5 |
| 6 h | 0.74 | 86.9 |
| 2 d | 6.27 | 9.1 | c) Storage behavior

The dry powder obtained in accordance with Preparation Example 1 b) was stored for 3½ months at room temperature and normal humidity. The particle sizes of the hydrosol were then redetermined. Compared with the fresh dry-powder sample, the particles were slightly larger.

The mean particle size was determined immediately after redispersion by quasi-elastic light scattering as 385 nm at a distribution range of ±42%. The mean of the volume distribution was determined by Fraunhofer diffraction as D(4,3)=0.88 μm, and the fines in the distribution were determined as 75.5%<1.22 μm. No noticeable increase in particle size was observed in the course of 4–6 hours (cf. Table 2).

TABLE 2

Particle sizes (Fraunhofer diffraction) of a chlorpyrifos hydrosol comprising 0.2% by weight of active ingredient, prepared by manually stirring the chlorpyrifos dry powder of b) into drinking water at room temperature, 3 1/2 months after spray-drying.

| Time after redispersion Immediately | D (4,3) [μm] 0.88 | Fines <1.22 μm 75.5 |
|---|---|---|
| 1 h | 0.74 | 86.8 |
| 2 h | 0.74 | 87.0 |
| 3 h | 0.74 | 87.1 |
| 4 h | 0.74 | 87.1 |
| 1 d | 3.33 | 15.8 | d) Differential Scanning Calorimetry (cf. FIG. 2 to FIG. 9)

Well-defined melting peaks were measured for the low-molecular-weight components chlorpyrifos, ascorbyl palmitate and lactose (FIGS. 2 to 4). The melt peak maximum of the active ingredient chlorpyrifos was determined as 45° C., which, as expected, was slightly above the value of 42.0 to 43.5° C. given in the literature (effect of the finite heating time). Broad bands of little structure were obtained for the two gelatins Gelita Sol® P and B 100 Bloom (FIGS. 5 and 6).

The DSC curves of the dry powder in accordance with Preparation Example 1 b) after storage for 3½ months (FIG. 7) and those of a formulation of identical composition which was prepared by grinding the crystalline starting components (FIG. 8) are compared in FIGS. 7 and 8. The grinding method gives 4 peaks, which can be assigned to the melting peaks of the crystalline components chlorpyrifos, ascorbyl palmitate and lactose (cf. FIGS. 2 to 4). These peaks are "grafted" onto the broad background of the gelatin signals. In contrast, only a broad rise and drop are observed in the measurement of the dry powder prepared in accordance with Example 1 (FIG. 7). What is particularly important is that the melting peak of the crystalline active ingredient chlorpyrifos is absent, which suggests that the active ingredient exists predominantly in the amorphous form in the nanoparticulate dry powder.

e) X-ray Wide-angle Scattering

FIG. 10 shows the scatter curves of active ingredient (top) and dry powder in accordance with Preparation Example 1 b) (middle). As confirmed by the interference diagram, which is distinguished by a series of well-defined interferences, the chlorpyrifos starting material is crystalline. In contrast, the scatter curve of the dry powder only shows diffuse, broad interference maxima as are typical for amorphous material. Accordingly, the active ingredient in the dry powder prepared in accordance with 1 b) is X-ray amorphous. This also applies to the adjuvants lactose and ascorbyl palmitate, which are otherwise crystalline.

Preparation Example 2

Preparation of a dry powder, for example chlorpyrifos (active ingredient content: approx. 25% by weight)

a) Preparation of the Micronizate 48 g of chlorpyrifos (purity: 96.5%) were stirred at 25° C. into a solution of 9.6 g of ascorbyl palmitate in 144 g of acetone giving a clear solution.

This solution was mixed with 79 g of acetone in the mixing chamber (6) at 156° C. The chlorpyrifos was precipitated in colloid-disperse form in such a way that, after a residence time of 3.4 seconds, the molecular disperse solution was fed into the mixing chamber (7). There, the material was mixed at 32° C. with 3320 g of an aqueous solution, brought to pH 9.2 using 1 N NaOH, of 14.1 g of gelatin B 100 Bloom, 60.5 g of Gelita Sol® P and 50 g of lactose in fully demineralized water. During the entire process, the pressure was limited to 30 bar by means of a valve (10) to prevent evaporation of the solvent. A white, cloudy colloid-disperse chlorpyrifos dispersion was obtained in the receiving vessel (11).

The mean particle size was determined as 252 nm by quasi-elastic light scattering, the distribution range being ±27%. The mean of the volume distribution was determined by Fraunhofer diffraction as D(4,3)=0.62 µm, and the fines in the distribution were determined as 99.8%<1.22 µm.

b) Drying of the Dispersion from (a) to a Nanoparticulate Dry Powder

Spray drying of the product from Preparation Example a) gave a free-flowing nanoparticulate dry powder. The active ingredient content in the powder was determined by chromotography as 24.67% by weight chlorpyrifos (in theory: 25.46% by weight). The dry powder dissolved in drinking water giving a white, cloudy dispersion (hydrosol).

The mean particle size was determined immediately after redispersion by quasi-elastic light scattering as 349 nm at a distribution range of ±55%. The mean of the volume distribution was determined by Fraunhofer diffraction as D(4,3)= 0.66 μm, and the fines in the distribution were determined as 96.4%<1.22 μm. No noticeable increase in particle size was observed in the course of 4–6 hours (cf. Table 3).

TABLE 3

Particle sizes (Fraunhofer diffraction) of a chlorpyrifos hydrosol comprising 0.2% of active ingredient, prepared by manually stirring the chlorpyrifos dry powder of b) into drinking water at room temperature on the day of spray drying.

| Time after redispersion | D (4,3) [μm] | Fines <1.22 μm |
|---|---|---|
| Immediately | 0.66 | 96.4 |
| 1 h | 0.65 | 96.6 |
| 2 h | 0.63 | 98.4 |
| 3 h | 0.65 | 96.5 |
| 4 h | 0.65 | 96.7 |
| 6 h | 0.73 | 87.4 |
| 2 d | 5.89 | 28.2 | c) Storage behavior

The dry powder obtained in accordance with Preparation Example 2 b) was stored for 3½ months at room temperature and normal humidity. The particle sizes of the hydrosol were then redetermined. Compared with the fresh dry-powder sample, the particles were slightly larger.

The mean particle size was determined immediately after redispersion by quasi-elastic light scattering as 345 nm at a distribution range of ±43%. The mean of the volume distribution was determined by Fraunhofer diffraction as D(4,3)= 0.89 μm, and the fines in the distribution were determined as 72.9%<1.22 μm. No noticeable increase in particle size was observed in the course of 4–6 hours (cf. Table 4).

TABLE 4

Particle sizes (Fraunhofer diffraction) of a chlorpyrifos hydrosol comprising 0.2% by weight of active ingredient, prepared by manually stirring the chlorpyrifos dry powder of b) into drinking water at room temperature, 3 1/2 months after spray-drying.

| Time after redispersion | D (4,3) [μm] | Fines <1.22 μm |
|---|---|---|
| Immediately | 0.89 | 72.9 |
| 1 h | 0.75 | 86.3 |
| 2 h | 0.74 | 87.0 |
| 3 h | 0.75 | 86.4 |
| 4 h | 0.75 | 86.2 |
| 1 d | 4.80 | 13.2 | d) Differential Scanning Calorimetry

FIG. 9 shows the DSC curve of the dry powder of Preparation Example 2. The absence of the melting peak of chlorpyrifos suggests that the active ingredient in the particles is still predominantly amorphous, even after storage.

e) X-ray Wide-angle Scattering

FIG. 10 shows the scatter curves of active ingredient (top) and dry powder in accordance with Preparation Example 2 b) (bottom). Again, the scatter curve of the dry powder only shows diffuse, broad interference maxima as are typical of amorphous material. Accordingly, the active ingredient in the dry powder prepared in accordance with 2 b) is in X-ray amorphous form.

Use Examples

The herbicidal action of the compositions according to the invention was demonstrated by greenhouse experiments:

The culture containers used were plastic flowerpots containing loaming sand with approximately 3.0% of humus as substrate. The seeds of the test plants were sown separately for each species.

In the case of herbicidal compositions, the application rates of active ingredients may vary, depending on the intended aim, the season, the target plants and the growth stage.

For the pre-emergence treatment, the compositions which are suspended in water were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active ingredients.

For the post-emergence treatment, the test plants were grown to a plant height of from 3 to 15 cm, depending on the plant habit, and only then treated with the compositions which had been suspended in water. To this end, the test plants were either sown directly and grown in the same containers, or they were first grown separately as seedlings and transplanted into the test containers a few days prior to treatment. For the treatment, the compositions which had been suspended in water were sprayed onto the leaves by means of finely distributing nozzles.

Depending on the species, the plants were kept at from 10–25° C. and 20–35° C., respectively. The test period extended over 2 to 4 weeks. During this time, the plants were tended, and their response to the individual treatments were evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific Name | Common Name |
|---|---|
| Triticum aestivum[a,b] | wheat |
| Zea mays[a,b] | corn |
| Glycine max[a] | soya |
| Alopecurus myosuroides | blackgrass |
| Avena fatua | wild oat |
| Bromus inermis | brown grass |
| Digitaria sanguinalis | large crabgrass |
| Echinochloa crus-galli | cockspur grass |
| Poa annua | annual bluegrass |
| Setaria faberi | giant foxtail |
| Brachiaria plantaginea | |
| Ischaemum rugosum | |
| Leptochloa dubia | |
| Amaranthus retroflexus | redroot pigweed |
| Chenopodium album | lamb's quarters |
| Galium aparine | catchweed bedstraw |
| Solanum nigrum | black nightshade |

[a] = target crop plant
[b] = as "volunteer wheat" or "volunteer corn" also a plant species to be controlled The compositions according to the invention allow very good control of undesired broad-leaved plants and grass weeds pre- or post-emergence.

We claim:

1. A solid crop protection composition consisting essentially of
   a) one or more predominantly amorphous solid crop protection active ingredients in nanoparticulate form having a solubility in water of less than 500 mg/l at 25° C.,
   b) a coating enclosing component (a), wherein the coating component is at least one surface-active polymeric colloid or at least one surface-active, amphiphilic compound, or a mixture thereof,
   c) optionally a stabilizer, and
   d) optionally a plasticizer
the mean diameter of the nanoparticulate active ingredient particles after redispersion being in the range from 0.05 to 0.8 μm.

2. The composition defined in claim 1, wherein the solubility in water of the crop protection active ingredients is less than 100 mg/l at 25° C.

3. The composition defined in claim 1, wherein the coating (b) consists essentially of gelatin.

4. The composition defined in claim 1, wherein the coating (b) consists essentially of a salt of a phenolsulfonic acid/urea/formaldehyde condensate.

5. A method of controlling undesirable vegetation, which comprises treating a crop plant, its environment and/or its seed with an effective amount of the composition defined in claim 1, wherein the crop protection active ingredient is a herbicidal crop protection active ingredient.

6. A method of controlling harmful fungi and pests, which comprises treating the harmful fungi or the pests, their environment, or the plants, areas, materials or spaces to be kept free from them, with an effective amount of the composition defined in claim 1 wherein the crop protection active ingredient is a fungicidal crop protection active ingredient or a crop protection active ingredient which acts against pests.

7. A method of regulating the growth of plants, which comprises treating the plants, their environment and/or their seeds with an effective amount of the composition defined in claim 1 wherein the crop protection active ingredient is a growth-regulatory crop protection active ingredient.

8. A process for the preparation of the composition defined in claim 1, which consists essentially of mixing a liquid formulation of the crop protection active ingredient with a liquid formulation of the coating component (b) and essentially drying the resulting coated crop protection active ingredient.

9. The method of claim 8, wherein the crop protection active ingredient is liberated from a salt thereof immediately prior to mixing.

10. The composition defined in claim 1, consisting essentially of from 0.5 to 75% by weight of the active ingredient component (a), from 10 to 70% by weight of the coating component (b), from 0 to 30% by weight of the stabilizer, and from 0 to 70% by weight of the plasticizer.

11. The composition defined in claim 1, wherein the coating component (b) is at least one polymer selected from the group consisting of biopolymers, modified biopolymers, synthetic anionic polymers, synthetic cationic polymers and synthetic neutral polymers.

12. The composition defined in claim 1, wherein the coating component (b) is at least one polymer selected from the group consisting of gelatin, pectin, chitosan, starch, dextrin, gum arabic, casein, caseinate, methylcellulose, carboxymethylcellulose, hydroxypropylcellulose, alginates, lignin derivatives, polyvinyl alcohol, polyvinylpyrrolidone, polyacrylic acid, polycarboxylates, polyethylene glycols, maleic anhydride/isobutene copolymers, vinyl-pyrrolidone/vinyl acetate copolymers, naphthalenesulfonic acid condensates, phenolsulfonic acid condensates, polyethylenimine, polyvinylamine, polyvinylformamide and partially hydrolyzed polyvinylformamide.

13. The composition defined in claim 1, wherein the amphiphilic compound of the coating component (b) is at least one member selected from the group consisting of anionic surfactants, cationic surfactants, non-ionic surfactants, zwitter-ionic surfactants and polymeric surfactants.

14. The composition defined in claim 11, wherein the amphiphilic compound of the coating component (b) is at least one member selected from the group consisting of soaps, alkyl sulfates, alkyl ether sulfates, alkyl/isoalkylsulfonates, alkylbenzenesulfonates, alkylnaphthalenesulfonate, alkylmethyl ester sulfonates, acyl glutamates, alkylsuccinic ester sulfonates, alkyl mono- and di-phosphates, sarcosinates, taurates, alkyltrimethylammonium halides and alkylsulfates, alkylpyridinium halides, dialkyldimethylammonium halides and alkylsulfates, alkoxylated animal and vegetable fats and oils, glycerol esters, fatty alcohol alkoxylates and oxoalcohol alkoxylates, fatty acid alkoxylates, alkylphenol alkoxylates, fatty amine alkoxylates, fatty acid amide alkoxylates, sugar surfactants, polyoxyethylene sorbitan fatty acid esters, alkyl polyglycosides, N-alkylgluconamides, alkylmethyl sulfoxides, alkyldimethylphosphine oxides, sulfobetaines, carboxybetaines, alkyldimethylamine oxides, (AB)x-, ABA or BAB, di- tri- and multi-block polymers AB comb polymers, perfluorinated surfactants, silicone surfactants, phospholipids, and amino acid surfactants.

15. The composition defined in claim 11, wherein the amphiphilic compound of the coating component (b) is at least one member selected from the group consisting of alkali metal, alkaline earth metal and ammonium salts of the fatty acids, alkyl sulfates, alkyl ether sulfates, alkyl- and isoalkylsulfonates, sodium dodecylbenzene sulfonate, alkylnaphthalenesulfonate, alkylmethyl ester sulfonates, acyl glutamates, alkylsuccinic ester sulfonates, alkyl mono- and diphosphates, sodium lauroylsarcosinate, taurates, alkyltrimethylammonium halides and alkylsulfates, alkylpyridinium halides, dialkyldimethylammonium halides and alkylsulfates, corn oil ethoxylates, castor oil ethoxylates, tallow fat ethoxylates, glycerol monostearate, fatty alcohol alkoxylates and oxoalcohol alkoxylates, oleic acid ethoxylates, isononylphenol ethoxylates, fatty amine alkoxylates, fatty acid amide alkoxylates, sorbitan fatty acid esters, polyoxyethylene sorbitan fatty acid esters, alkyl polyglycosides, N-alkylgluconamides, alkylmethyl sulfoxides, tetradecyldimethylphosphine oxide, sulfobetaines, carboxybetaines, tetradecyldimethylamine oxide, polyethylene oxide-block-polypropylene oxide, polystyrene-block-polyethylene oxide, polymethacrylate- and polyacrylate-comb-polyethylene oxide, perfluorinated surfactants, silicone surfactants, lecithin and N-lauroylglutamate.

16. A method of protecting crop plants, which comprises treating the crop plants their environment or their seeds with an effective amount of a solid composition consisting essentially of
   a) one or more predominantly amorphous solid crop protection active ingredients in nanoparticulate form having a solubility in water of less than 500 mg/l at 25° C. and
   b) a coating enclosing component (a), wherein the coating component is at least one surface-active polymeric colloid or at least one surface-active, amphiphilic compound, or a mixture thereof, or a dispersion thereof wherein the mean diameter of the nanoparticulate active ingredient particles after redispersion is of from 0.05 to 0 $\mu$m.

17. The method of claim 16, wherein the coating component (b) is at least one surface-active polymeric colloid or at least one surface-active, amphiphilic compound, or a mixture thereof.

18. The method of claim 16, wherein the active ingredient component is at least one active ingredient selected from the group of fungicidal ingredients, herbicidal ingredients, insecticidal ingredients, acaricidal ingredients and plant-growth regulating ingredients.

* * * * *